United States Patent
Chow et al.

(10) Patent No.: US 11,466,030 B2
(45) Date of Patent: Oct. 11, 2022

(54) VISIBLE LIGHT ACTIVATED PRINTING INK

(71) Applicant: Nano and Advanced Materials Institute Limited, Hong Kong (HK)

(72) Inventors: Pui Keong Chow, Hong Kong (HK); Faan Fung Hung, Hong Kong (HK); Chenmin Liu, Hong Kong (HK); Chi Ho Kwok, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 311 days.

(21) Appl. No.: 16/908,685

(22) Filed: Jun. 22, 2020

(65) Prior Publication Data

US 2020/0399287 A1  Dec. 24, 2020

Related U.S. Application Data

(60) Provisional application No. 62/865,332, filed on Jun. 24, 2019.

(51) Int. Cl.
| | |
|---|---|
| *C07D 498/20* | (2006.01) |
| *C07D 491/06* | (2006.01) |
| *C09D 11/102* | (2014.01) |
| *C09D 11/037* | (2014.01) |
| *C08K 5/01* | (2006.01) |
| *C08K 5/3437* | (2006.01) |

(52) U.S. Cl.
CPC ........ *C07D 498/20* (2013.01); *C07D 491/06* (2013.01); *C09D 11/037* (2013.01); *C09D 11/102* (2013.01); *C08K 5/01* (2013.01); *C08K 5/3437* (2013.01)

(58) Field of Classification Search
CPC ........................... C07D 498/20; C07D 491/06
See application file for complete search history.

(56) References Cited

U.S. PATENT DOCUMENTS 4,929,693 A * 5/1990 Akashi .................. C08F 26/06
359/241

FOREIGN PATENT DOCUMENTS

| CN | 103965691 A | 8/2014 |
|---|---|---|
| WO | 2012083469 A1 | 6/2012 |
| WO | 2017112507 A2 | 6/2017 |

OTHER PUBLICATIONS

Jingjing Xu et al., "Visible-Light-Driven "On"/"Off" Photochromism of a Polyoxometalate Diarylethene Coordination Complex", Journal of the American Chemical Society, 2018, 140, pp. 10482-10487.
Tuyoshi Fukaminato et al., "Molecular Design Strategy toward Diarylethenes That Photoswitch with Visible Light", Journal of the American Chemical Society, 2014, 136, pp. 17145-17154.

* cited by examiner

*Primary Examiner* — Khanh T Nguyen
(74) *Attorney, Agent, or Firm* — Idea Intellectual Limited; Margaret A. Burke; Sam T. Yip

(57) ABSTRACT

A visible light activated ink that produces a color change when exposed to visible light is provided. The ink includes a visible light activated photochromic compound, one or more binders, additives including one or more surfactants, and a solvent. The visible light activated ink is substantially colorless in the as-deposited state and requires a visible light intensity of approximately 300 W/m² or greater at a wavelength of approximately 400-700 nm to produce a color change.

17 Claims, 7 Drawing Sheets

VISIBLE LIGHT ACTIVATED PRINTING INK

CROSS-REFERENCE TO RELATED APPLICATIONS

This is a non-provisional application claiming priority from the U.S. provisional patent application Ser. No. 62/865,332 filed Jun. 24, 2019, and the disclosure of which is incorporated herein by reference in its entirety.

FIELD OF THE INVENTION

The present invention relates to the field of printing ink, and more particularly, to a printing ink that is activated by visible light, suitable for use in security marking, or anti-counterfeit measures.

BACKGROUND

Photochromism is the reversible transformation of a compound/molecule between two forms, A and B, with different absorption spectra, activated by absorption of radiation of a certain range of wavelength.

Photochromic compounds, such as spiropyran, spirooxazine and naphthopyran, can be activated by UV light source, either UVA or UVB, to display color changes. The wavelength of such light sources is typically about 320 nm to 390 nm. Upon absorption of UV light, the structure of photochromic compound changes and switches from the colorless ring-closed form to the colored ring-opened form. The applications of this color changing effect include smart books, product packaging, toys, security marking such as secret ink, secret marks and anti-counterfeit packaging.

Photochromic printing inks may be used as secret inks for the security of the documents. As deposited, the ink is colorless and no mark is visible to the human eye. After irradiation by a UV light source, the conformation change of photochromic compounds in the inks changes and the printed mark displays a color. However, the major limitation of the existing photochromic compounds is the light source. There are safety concerns relating to the use of UV light. For example, UV light sources have been linked to mutagenesis of human cells. Further, UV light sources are not typically found in offices and homes. In addition to issue regarding the UV light source, the existing photochromic compounds typically have a poor bleaching time changing from color to colorless upon removal of the activating light source.

In view of the disadvantages of the existing photochromic compounds in printing ink, there is a need for developing photochromic compounds which is able to be activated in visible light and having a rapid bleaching time changing from a colored to colorless state. Such new photochromic compounds could be used in printing inks for security and anti-counterfeit measures.

SUMMARY OF THE INVENTION

A visible light activated ink that produces a color change when exposed to visible light is disclosed. The ink includes a visible light activated photochromic compound in an amount of approximately 0.2 to 20 weight percent and one or more binders in an amount of approximately 10 to 45 weight percent. Additives in an amount from approximately 2 to 8 weight percent include one or more surfactants. A solvent makes up approximately 35 to 70 weight percent. The visible light activated ink is substantially colorless in the as-deposited state and requires a visible light intensity of approximately 300 $W/m^2$ or greater at a wavelength of approximately 400-700 nm to produce a color change.

In a first embodiment of the first aspect of the present invention, there is provided a visible light activated ink where the photochromic compound is preferably selected from one or more of π-extended conjugation heterocyclic compound analogues of naphthopyran, benzopyran, spirooxazine, spiropyran, fulgide, diarylethene, perimidine-spirocyclohexadienone, or mixtures thereof.

In a second embodiment of the first aspect of the present invention, there is provided a visible light activated ink where the binder is selected from one or more polymers.

In a third embodiment of the first aspect of the present invention, there is provided a visible light activated ink where the surfactants are selected from one or more of one or more of polyethylene glycol sorbitan monolaurate, polyoxyethylenesorbitan monolaurate.

In a fourth embodiment of the first aspect of the present invention, there is provided a visible light activated ink where the solvent is selected from water, alcohols, polyols, esters, ketones, glycerol, vegetable oils, or mixtures thereof.

In a fifth embodiment of the first aspect of the present invention, the π-extended conjugation heterocyclic compounds of naphthopyran is represented by following formula:

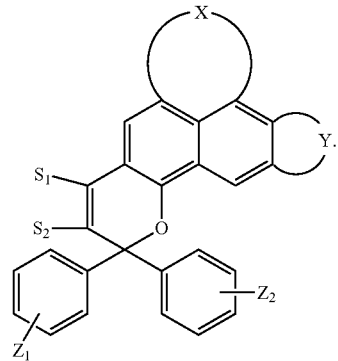

In a sixth embodiment of the first aspect of the present invention, the π-extended conjugation heterocyclic compounds of naphthopyran is represented by following formula:

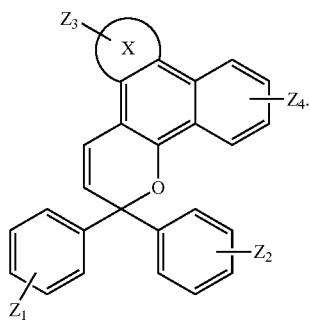

In a seventh embodiment of the first aspect of the present invention, the π-extended conjugation heterocyclic compounds of spirooxazine is represented by following formula:

In an eighth embodiment of the first aspect of the present invention, the π-extended conjugation heterocyclic compounds of spiropyran is represented by following formula:

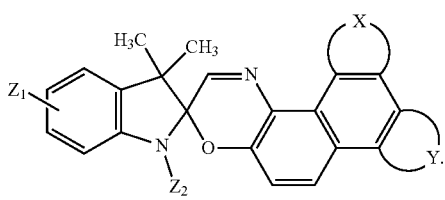

In a ninth embodiment of the first aspect of the present invention, the π-extended conjugation heterocyclic compounds of fulgide is represented by following formula:

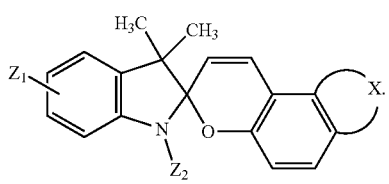

In a tenth embodiment of the first aspect of the present invention, the π-extended conjugation heterocyclic compounds of diarylethene is represented by one of the following formula:

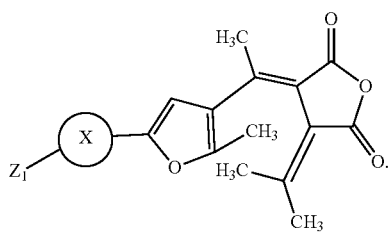

In an eleventh embodiment of the first aspect of the present invention, the π-extended conjugation heterocyclic compounds of perimidinespirocyclohexadienone is represented by following formula:

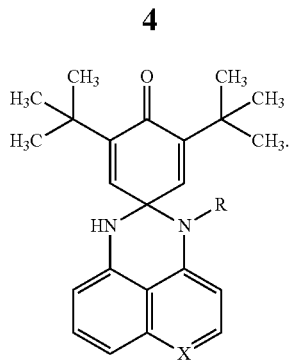

An ink composition selected from an inkjet ink composition, offset printing ink composition or coating ink composition is provided, wherein the ink composition comprises the visible light activated ink of the present invention, and optionally one or more resins.

In one embodiment of the ink composition, the visible light activated ink is selected from a naphthopyran analogue having the following formula:

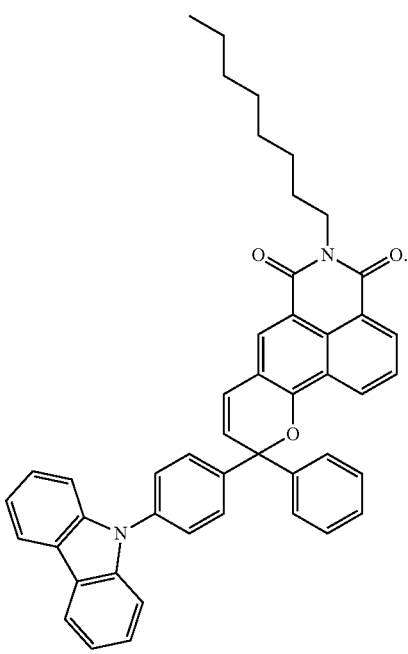 [SMILES: CCCCCCCCN1C(=O)c2cccc3c4c(cc(c23)C1=O)C=CC(c1ccccc1)(c1ccc(-n2c3ccccc3c3ccccc32)cc1)O4]

In another embodiment of the ink composition, the visible light activated ink is selected from a spirooxazine analogue having the following formula:

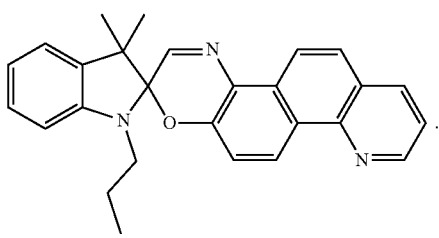 [SMILES: CCCN1c2ccccc2C(C)(C)C12C=Nc1c(ccc3c1ccc1cccnc13)O2]

In an embodiment, the visible light activated photochromic compound in the inkjet ink composition is in an amount of approximately 0.2 to 3 weight percent; the inkjet ink composition further comprises the binder in an amount of approximately 30 to 40 weight percent selected from diethylene glycol monoethyl ethyl acetate and the solvent in an amount of approximately 50 to 70 weight percent selected from ethyl acetate.

In other embodiment, the visible light activated photochromic compound in the offset printing ink composition is in an amount of approximately 1 to 20 weight percent; the offset printing ink composition further comprises the additives in an amount of approximately 2 to 8 weight percent selected from one or more of polyethylene wax, rheological additives and Drier; the solvent in an amount of approximately 10 to 30% weight percent selected from one or more of linseed oil, soybean oil, tung oil and ethyl acetate; the one or more resins selected from rosin modified phenolic resin, polyurethane-based resin, rosin modified maleic acid resin, long-oil alkyd resin and mineral oil, in an amount of 25 to 90%.

In an embodiment, the visible light activated photochromic compound in the coating ink composition is in an amount of approximately 0.3 to 5 weight percent; and the coating ink composition further comprises the solvent in an amount of approximately 10 to 55 weight percent selected from ethyl acetate; and the one or more resins is selected from polyurethane-based resin in an amount of 80 to 90 weight percent being doped with the visible light activated photochromic compound.

BRIEF DESCRIPTION OF THE DRAWINGS

Embodiments of the present invention are described in more detail hereinafter with reference to the drawings, in which.

DEFINITIONS

Figure 1:
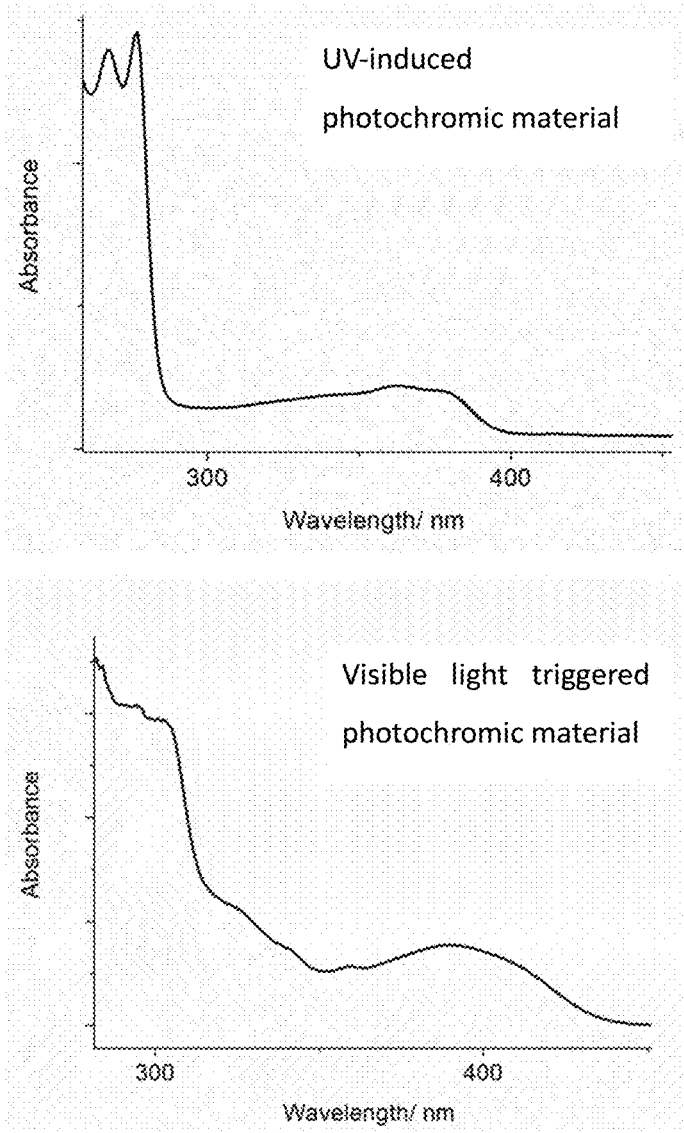
FIG. 1 illustrates the absorption spectrum of visible light activated photochromic material and UV-induced photochromic material.

The term "bleaching time" used herein, refers to the time interval of the activation of photochromic compounds transforming from color to colorless.

Alkyl

The term "alkyl" as used herein includes reference to an unbranched or branched chain alkyl moiety having 1, 2, 3, 4, 5, 6, 7, 8, 9, 10, 11, 12, 13, 14, 15, 16, 17, 18, 19 or 20 carbon atoms.

Alkoxy

The terms "alkoxy" as used herein include reference to —O-alkyl, wherein alkyl is unbranched or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1, 2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes F, Cl, Br or I.

DETAILED DESCRIPTION

1. Development of Visible Light Activated Photochromic Compounds

In order to create photochromic compounds that have color-changing properties in response to visible light activation, various photochromic compounds that color change in response to UV light were selected as starting materials. Examples of starting materials include naphthopyran, benzopyran, spirooxazine, spiropyran, fulgide, diarylethene, and perimidinespirocyclohexadienone In the present invention, the absorption spectrum of these starting material photochromic compounds was adjusted to the visible region through two techniques: (A) extending the π-conjugation of the molecules, either by attachment of electronic withdrawing groups and/or extending the π-surface to the molecules and (B) incorporation of a heterocycle(s) to the molecule. To extend the π-surface, a selected starting molecule is engineered with its benzene ring replaced with a highly-extended ring structure. As a result of this modification, the HOMO-LUMO band gap (highest occupied molecular orbital/lowest unoccupied molecular orbital), corresponding to a π→π* transition upon light absorption, is sufficiently narrowed. Furthermore, incorporating a heterocycle(s) with N, O, or S typically results in more delocalizing electrons in the aromatic ring. This also lowers the energy of the π→π* transition, resulting in red-shifted absorptions.

2. Examples of Molecules Obtained by the Above Approach:

Several novel compounds are formed using the above approaches and are listed below:

A π-extended conjugation heterocyclic compound of naphthopyran is formed that changes color in response to visible light and is represented by the following formula:

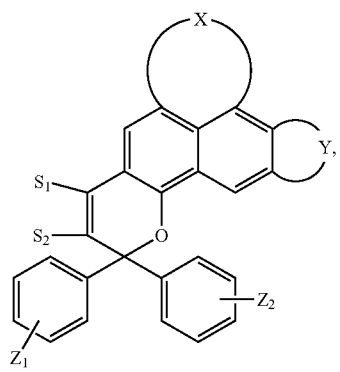

wherein X is selected from 1-alkylpiperidine-2,6-dione, 3,4-Dihydropyrido[1,2-a]benzimidazol-1(2H)-one, glutaric anhydride or 1-arylpipidine-2,6-dione;

Y is selected from hydrogen, benzene, naphthalene, fluorene, anthracene, phenanthrene, pyrene, tetracene, chrysene, pyrrolidine, pyrrole, pyrazole, carbazole, imidazole, benzimidazole, piperidine, indoline, pyridine, pyrazine, thiophene, benzo[b]thiophene, furan, benzofuran or any of their substituted analogues;

$Z_1$ and $Z_2$ are independently selected from hydrogen, halo, halo alkyl, alkoxy, ester, ether, imide, diimide, nitro, cyano, carbonyl, or sulfonyl group;

$S_1$ and $S_2$ are independently selected from hydrogen, halo, halo alkyl, ester, ether, imide, diimide, nitro, cyano, carbonyl, sulfonyl, benzene, naphthalene, fluorene, pyrrolidine, pyrrole, pyrazole, carbazole, imidazole, benzimidazole, piperidine, indoline, pyridine, pyrazine, thiophene, benzo[b]thiophene, furan, benzofuran or acetylene or any of their substituted analogues.

A π-extended conjugation heterocyclic compound of naphthopyran is formed that changes color in response to visible light and is represented by the following formula:

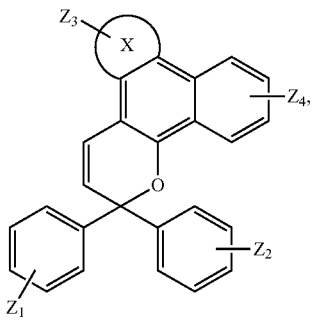

wherein X is selected from 3,3-di-alkyl-1,2-dihydroindene, benzene, naphthalene, fluorene, anthracene, phenanthrene, pyrene, tetracene, chrysene, pyrrolidine, pyrrole, pyrazole, carbazole, imidazole, benzimidazole, piperidine, indoline, pyridine, pyrazine, thiophene, benzo[b]thiophene, furan, benzofuran or any of their substituted analogues;

$Z_1$, $Z_2$, $Z_3$ and $Z_4$ are independently selected from hydrogen, halo, halo alkyl, alkoxy, ester, ether, imide, diimide, nitro, cyano, carbonyl, or sulfonyl group.

A spirooxazine analogue is represented by following formula:

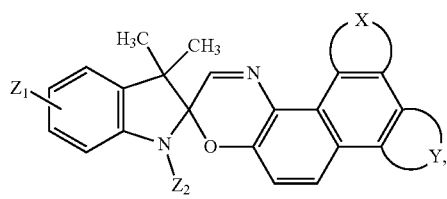

wherein X is selected from hydrogen, benzene, naphthalene, fluorene, anthracene, phenanthrene, pyrene, tetracene, chrysene, 1,10-phenanthroline, quinolone, pyrrolidine, pyrrole, pyrazole, imidazole, benzimidazole, piperidine, indoline, pyridine, pyrazine, thiophene, benzo[b]thiophene, furan or benzofuran;

Y is selected from 1,10-phenanthroline, pyrene, tetracene, chrysene, pyrrolidine, pyrrole, pyrazole, imidazole, benzimidazole, piperidine, indoline, pyridine, pyrazine, thiophene, benzo[b]thiophene, furan or benzofuran;

$Z_1$ is selected from hydrogen, halo, halo alkyl, ester, imide, diimide, nitro, cyano, carbonyl, or sulfonyl group; and $Z_2$ is selected from unbranched or branched alkyl chains, benzene, phenol, anisole, or crown ether.

A spiropyran analogue is represented by following formula:

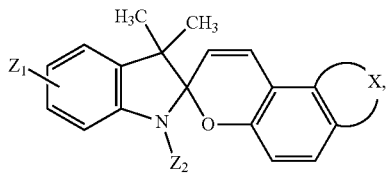

wherein X is selected from pyrazine, 1,10-phenanthroline, pyrene, tetracene, chrysene, pyrrolidine, pyrrole, pyrazole, imidazole, benzimidazole, piperidine, indoline, pyridine, thiophene, benzo[b]thiophene, furan, benzofuran, or quinoline;

$Z_1$ is selected from hydrogen, halo, halo alkyl, ester, imide, diimide, nitro, cyano, carbonyl, or sulfonyl group; and $Z_2$ is selected from unbranched or branched alkyl chains, benzene, phenol, anisole, or crown ether.

A fulgide analogue is represented by following formula:

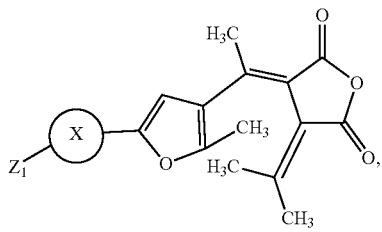

wherein X is selected from naphthalene, fluorene, anthracene, phenanthrene, pyrene, tetracene, chrysene, 1,10-phenanthroline, quinolone, pyrrolidine, pyrrole, pyrazole, imidazole, benzimidazole, piperidine, indoline, pyridine, pyrazine, thiophene, benzo[b]thiophene, furan or benzofuran; and $Z_1$ is selected from hydrogen, halo, halo alkyl, ester, imide, diimide, nitro, cyano, carbonyl, or sulfonyl group.

A diarylethene analogue is represented by following formula:

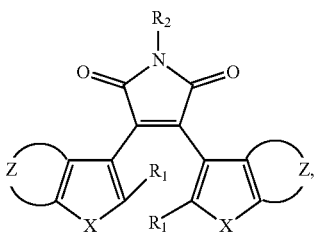

wherein X is selected from S, $SO_2$, N, O, P-aryl or O=P-aryl;

$R_1$ is selected from hydrogen atom, alkyl or alkoxy group;

$R_2$ is selected from hydrogen atom, alkyl, benzene, naphthalene, fluorene, anthracene, phenanthrene, pyrene, tetracene, chrysene, pyrrolidine, pyrrole, pyrazole, imidazole, benzimidazole, piperidine, indoline, pyridine, pyrazine, thiophene, benzo[b]thiophene, furan or benzofuran;

Z is selected from hydrogen atoms, benzene, substituted benzene containing halogen, halo alkyl, ester, imide, diimide, nitro, cyano, carbonyl, or sulfonyl group.

A diarylethene analogue is represented by following formula:

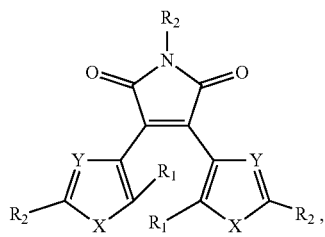

wherein X is selected from S, $SO_2$, N, O, P-aryl or O=P-aryl;

Y is selected from H, S, N, or O atom;

$R_1$ is selected from hydrogen atom, alkyl or alkoxy group;

$R_2$ is selected from hydrogen atom, alkyl, benzene, naphthalene, fluorene, anthracene, phenanthrene, pyrene, tetracene, chrysene, pyrrolidine, pyrrole, pyrazole, imidazole, benzimidazole, piperidine, indoline, pyridine, pyrazine, thiophene, benzo[b]thiophene, furan or benzofuran;

Z is selected from hydrogen atoms, benzene, substituted benzene containing halogen, halo alkyl, ester, imide, diimide, nitro, cyano, carbonyl, or sulfonyl group.

A perimidinespirocyclohexadienone analogue is represented by following formula:

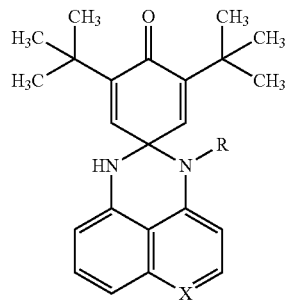

wherein X is selected from CH or N; and

R is selected from hydrogen atom, aryl, arylalkyl, substituted aromatic cycles containing halogen, halo alkyl, ester, imide, diimide, nitro, cyano, carbonyl, or sulfonyl group.

The above compounds may be activated by visible light, that is, they change from colorless to colored when excited by visible light. Noting that normal levels of ambient light are typically not sufficient to induce the color change, instead, more concentrated visible light sources having an intensity of approximately 300 W/m² are used to induce the color change. This level of intensity may be obtained from an ordinary flashlight or, for example, a flash light associated with a mobile phone.

3. Photo-Physical Properties of Visible Light Activated Photochromic Materials

Figure 2:
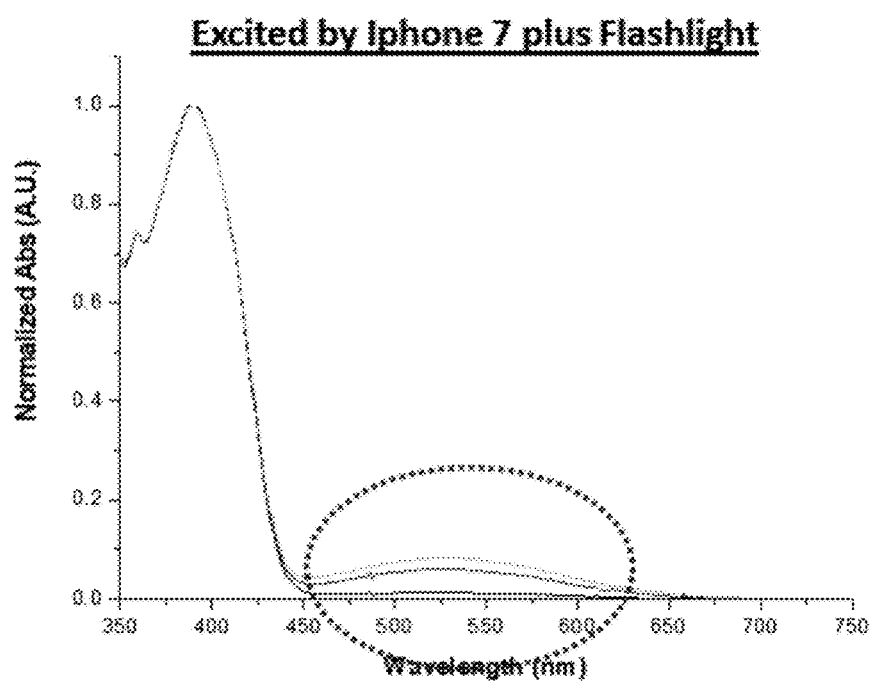
FIG. 2 illustrates broad absorption centered at 529 nm of visible light activated photochromic material.

The π-extended conjugation heterocyclic compound of naphthopyran of formula:

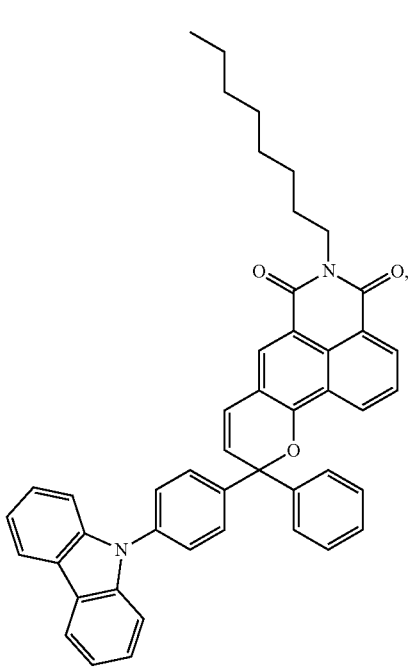 [SMILES: CCCCCCCCN1C(=O)c2cccc3c4c(cc(c23)C1=O)C=CC(c1ccccc1)(c1ccc(-n2c3ccccc3c3ccccc32)cc1)O4]

was dissolved in a hexane solution ($2\times10^{-5}$M). By exciting the solution with a mobile flashlight (model: iPhone 7 plus, emitting at an intensity of at least 300 W/m$^2$), the solution changed from colorless to purple immediately. As shown in FIG. 1, relating to a colorless form, the naphthopyran analogue showed intense absorption in a visible light region (400-700 nm), centered at approximately 529 nm (FIG. 2). Such absorptions are not found in the spectrum of UV-activated conventional photochromic materials as seen in FIG. 1.

Figure 3:
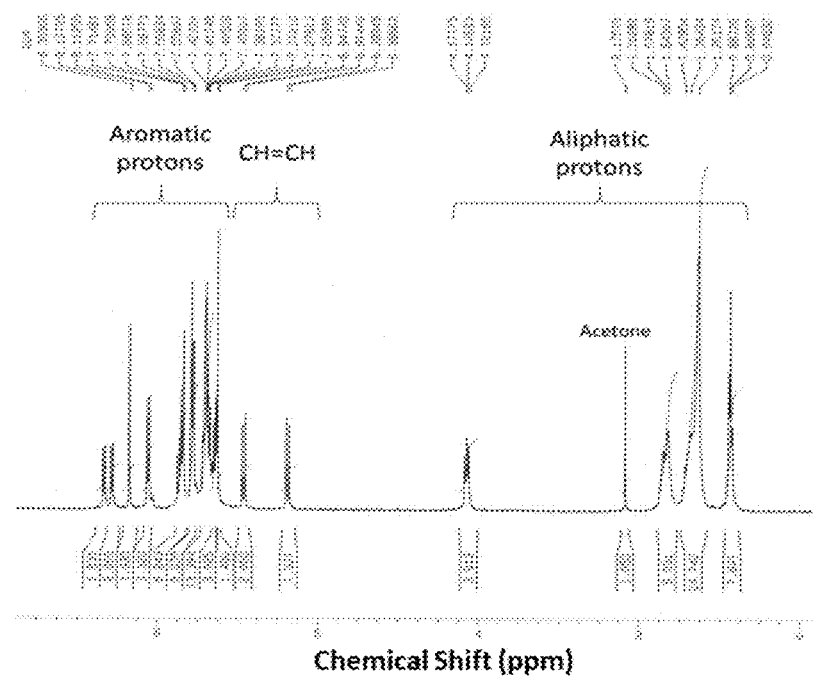
FIG. 3 illustrates the NMR result for a modified naphthopyran material, Vis-exNap-1.

Structure Characterization by NMR:

FIG. 3 shows the NMR result for the naphthopyran analogue described above. The molecule has been found to contain 21 aromatic protons, 2 sp$^2$ protons from a double bond and 17 aliphatic protons.

4. Ink Compositions with Visible Light Activated Photochromic Compounds

The inventive photochromic compounds may be incorporated into a variety of ink compositions that may be used for security and anti-counterfeit products. In one aspect, the photochromic compounds may be incorporated into an ink jet printing ink. It is noted that the compounds may be added to the ink as compounds or mixed in a carrier resin and dispersed in the ink. Ink jet printing inks broadly include a solvent (water-based solvent or an organic-based solvent), a binder, a surfactant, and the photochromic material. They are without conventional ink dyes and pigments. Thus, they are colorless when printed, exhibiting color change only when activated by visible light having an intensity of approximately 300 W/m$^2$ or greater. In an exemplary embodiment, the ink jet printing inks include approximately 0.2 to 20 weight percent photochromic compound, approximately 10-25 weight percent binder, approximately 2-12 weight percent of other additives, including surfactant, and approximately 35-65 weight percent solvent.

In another aspect, other inks such as offset printing, screen printing, gravure printing, and flexographic printing inks may be formulated. These inks may be formed using the inventive photochromic materials. In general, this second class of inks is higher viscosity, typically using an oil as the solvent and often a higher percentage of binder. High viscosity inks may include approximately 0.2 to 20 percent of photochromic material, approximately 10-35 percent of binder, approximately 2-8 percent additives (including surfactant) and approximately 40-60 weight percent of a solvent, typically a high-viscosity oil-based solvent.

Coating ink may be formulated using the present photochromic materials. This class of inks has a higher viscosity than the ink jet inks. In an embodiment, the coating ink is formulated by dissolving approximately 0.4 to 3 weight percent of the photochromic material in 45 to 89 weight percentage of polymer resin followed by dilution with approximately 10 to 54 weight percent of one or a mixture of solvent(s).

In general, solvents may include water, alcohols, polyols, esters, ketones, glycerol, vegetable oils. The binders may be selected from polymeric binders including rubbers, polyvinyl alcohol, styrene acrylic latex, polyurethane, acrylates, vinyl acrylates, vinyl acetates, methacrylates, styrene, acrylamides, methacrylamides, alkyds, phenolics, nitrocellulose, polyamides, poly(vinyl acetate), poly(vinyl butyral), or polyacrylics. The polymer may be formed in an emulsion with the solvent. The amount is selected to produce the desired viscosity, with the desired viscosity changing depending on the printing method and the selected substrate.

Additives may include surfactants such as nonionic detergents, surfactants such as polyethylene glycol sorbitan monolaurate, polyoxyethylenesorbitan monolaurate (commercially available as TWEEN 20), humectants, stabilizers, thickeners such as ethylene glycol, glycerol or diethylene glycol, adhesion promoters, buffers, antibacterial agents, dispersants, and antioxidant.

Examples

1. Inkjet Ink Composition:

An experimental inkjet composition is composed of with 0.5-3 wt % naphthopyran analogue, 50-70 wt % ethyl acetate as a solvent and 30-40 wt % diethylene glycol monoethyl ethyl acetate. The photochromic compound is initially dissolved in a small amount of ethyl acetate, approximately 0.5 ml of ethyl acetate for a 20 ml formula.

The naphthopyran analogue is the following formula:

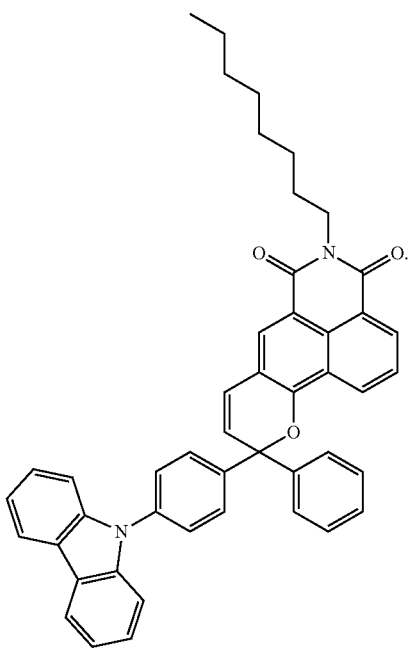 [SMILES: CCCCCCCCN1C(=O)c2cccc3c4c(cc(c23)C1=O)C=CC(c1ccccc1)(c1ccc(-n2c3ccccc3c3ccccc32)cc1)O4]

Figure 4:
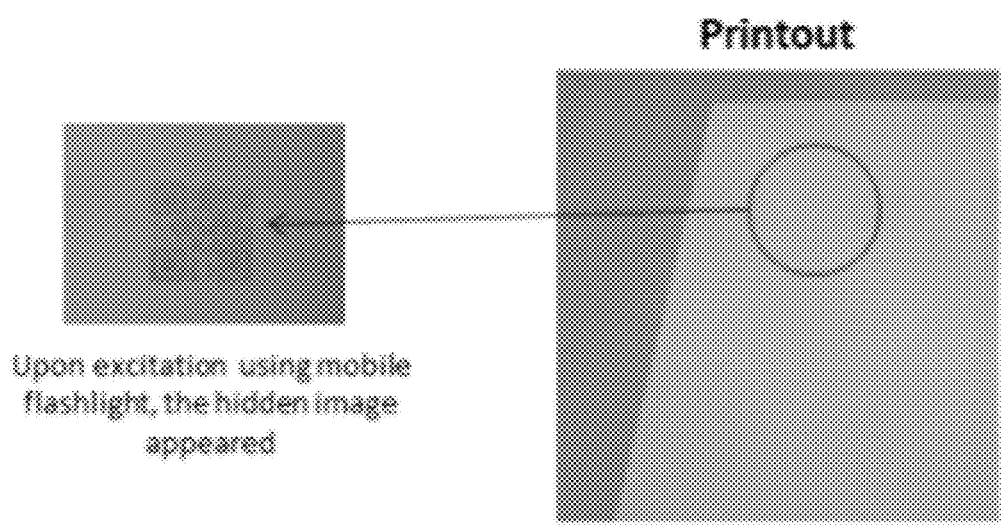
FIG. 4 illustrates the appearance of the purple security mark after activating by mobile flashlight.

This ink was printed in the form of a security mark on ordinary printer paper using an inkjet printer; the printout showed almost no recognizable mark as the ink is colorless, without conventional dyes or pigments. A colorimeter was used to detect the color of mark on the printout as printed, and a total color different versus a white background (ΔE, LAB color system) of 3.1 was measured. After exciting the hidden and colorless security mark on the printout paper using mobile flashlight with a visible light intensity of at least 300 W/m², the purple security mark appeared (FIG. 4). The excited security and colorless mark can be recognized by a device equipped with a detector for at least approximately 7 minutes. After turning off the mobile flashlight, the colorized image fades to substantially colorless in approximately 10 minutes.

2. Offset Printing Ink Composition

Two more visible light activated photochromic offset inks have been formulated. Offset Resin 1 and Offset Resin 2 have been used for Formulation 1 and Formulation 2 respectively. Formulation 1 contained relatively higher content of visible light activated photochromic material in 2-10 wt % while Formulation 2 contained 1-3 wt %. Both used the photochromic material of the formula:

Offset Resin 1 included a mixture of linseed oil, soybean oil, and tung oil (20-40 weight %), rosin modified phenolic resin (25-50 weight %), mineral oil (15-30 weight %), polyethylene wax (0.2-2 weight %) and Drier (0.5-2 weight %). Offset Resin 2 included a mixture of PU based resin (80-90 weight %), ethyl acetate (2-10 weight %), and other rheological additives (1-10 weight %).

Figure 5:
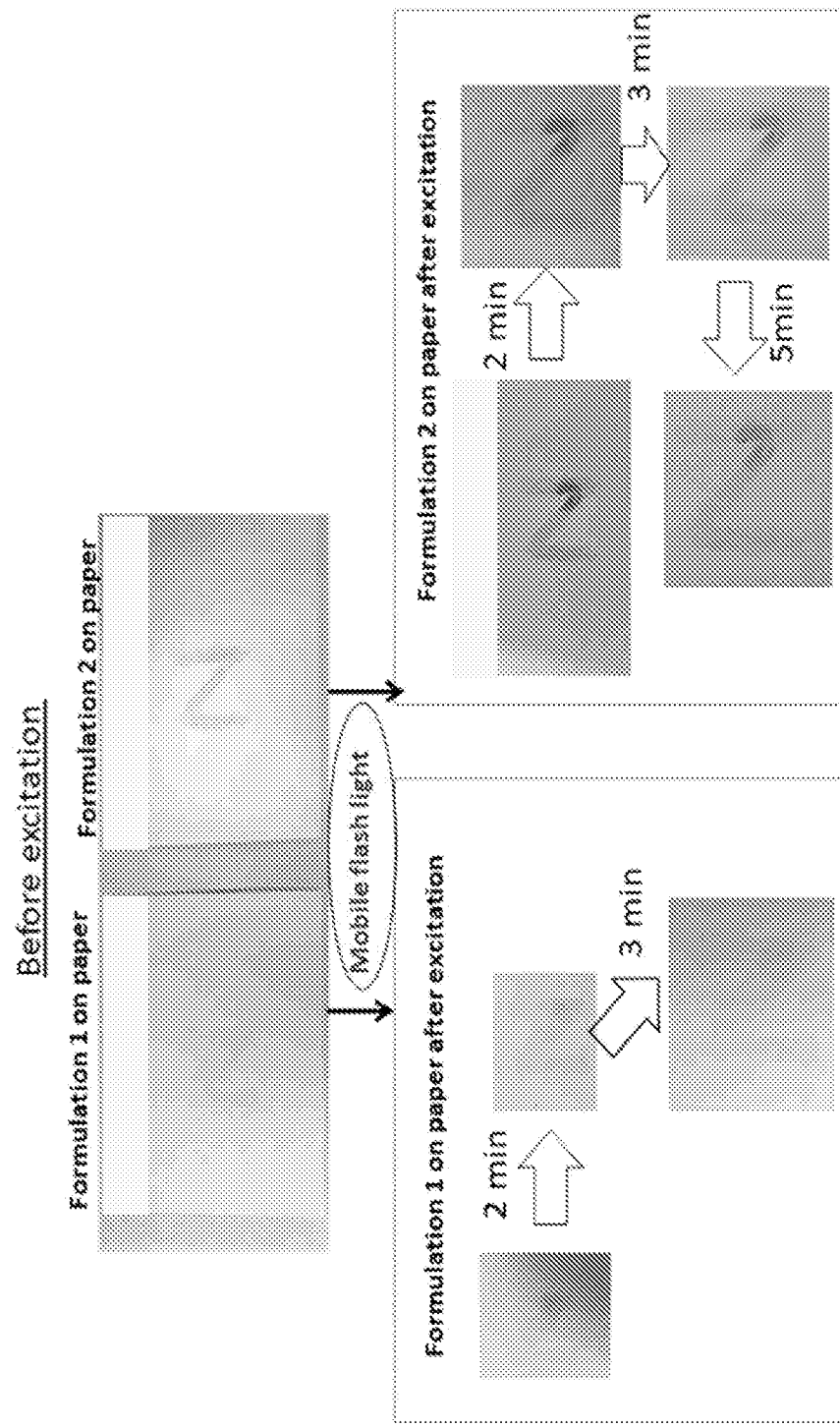
FIG. 5 illustrates features of two visible light activated photochromic offset inks.

Due to the different chemical nature of Offset Resin 1 and Offset Resin 2, the Formulation 1 and Formulation 2 showed different photochromic properties; as shown in FIG. 5, the printed mark of Formulation 1 lasted for about 3 minutes after mobile flashlight excitation. In contrast, the printed mark lasted for more than 5 minutes without obvious fade out after mobile flashlight excitation. This suggested the photochromic properties of the visible light activated photochromic materials can be greatly manipulated using different formulation recipe.

Other examples of offset resin: Offset Resin 3 included a mixture of linseed oil, soybean oil, and tung oil (10-25 weight %), rosin modified maleic acid resin (25-40 weight %), long-oil alkyd resin (10-20 weight %), mineral oil (15-30 weight %), polyethylene wax (0.2-2 weight %) and Drier (0.5-2 weight %). Offset Resin 4 included modified vegetable oil (20-40 weight %), modified hydrocarbon resin (25-50 weight %), mineral oil (15-30 weight %), polyethylene wax (0.2-2 weight %) and Drier (0.5-2 weight %).

3. Coating Ink for Fabrication of a Transparent, Visible Light-Triggered, Color-Changing Layer on Plastics.

A kind of coating ink was formulated by dispersing a naphthopyran analogue in polyurethane resin with dopant concentration of 0.5 to 3 weight percent. The resulting mixture was diluted with approximately 10 to 55 weight percent of ethyl acetate to make the coating ink. The coating ink was applicable on the surface of plastic such as PET. One coating ink contained approximately 1 weight percent of naphthopyran analogue with the formula:

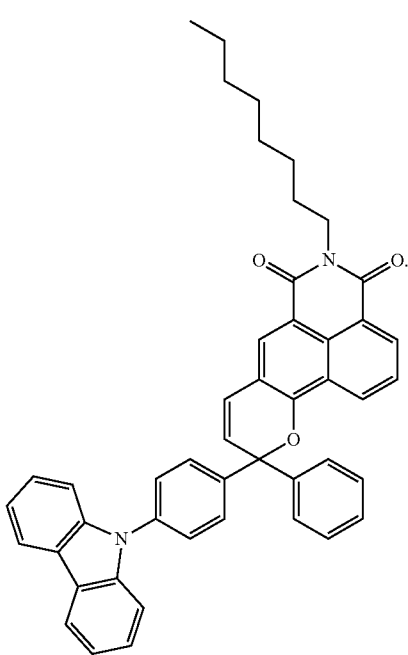 [SMILES: CCCCCCCCN1C(=O)c2cccc3c4c(cc(c23)C1=O)C=CC(c1ccccc1)(c1ccc(-n2c3ccccc3c3ccccc32)cc1)O4]

Figure 7:
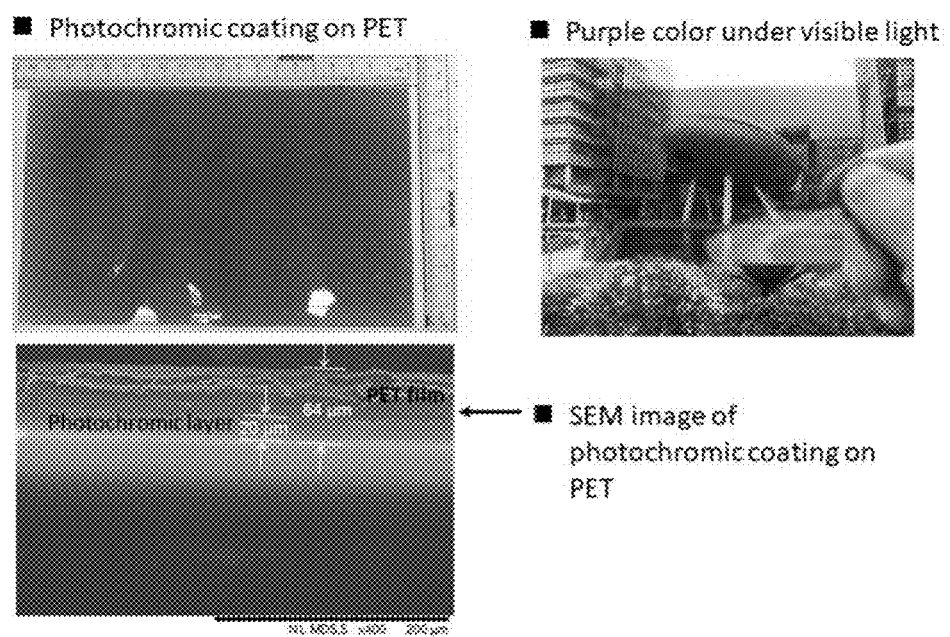
FIG. 7 illustrates the transparent photochromic coating of visible light activated photochromic materials.

As shown in FIG. 7, the coating ink was coated on PET, forming a transparent thin film with thickness of about 20 microns and transmittance of 90%. Under visible light, the film show purple color with the transmittance of 38%

Another example of coating ink was formulated by dispersing a spirooxazine analogue having the following formula:

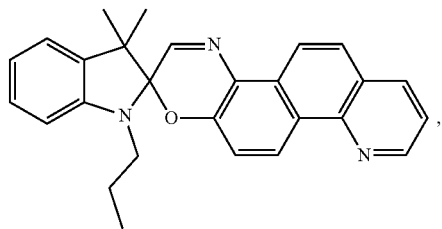 [SMILES: CCCN1c2ccccc2C(C)(C)C12C=Nc1c(ccc3c1ccc1cccnc13)O2]

in polyurethane resin with dopant concentration of 0.3 to 5 weight percent. The resulting mixture was diluted with approximately 10 to 55 weight percent of ethyl acetate to make to coating ink. The coating ink was applicable on surface of plastic such as PET.

Effect on Molecular Engineering on Photochromic Properties

Figure 6:
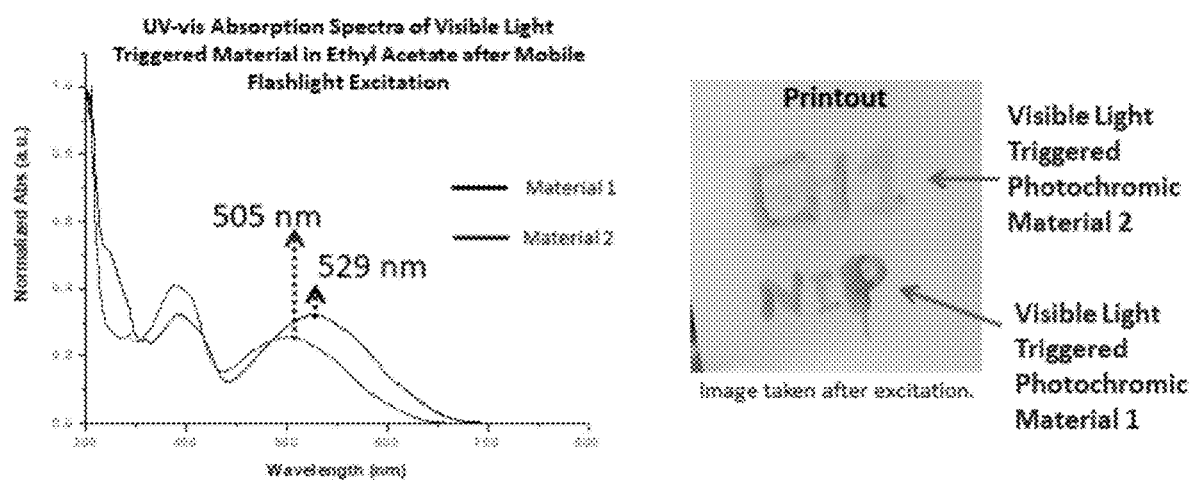
FIG. 6 illustrates different absorption spectrums of two visible light activated photochromic materials.

The two visible light activated photochromic materials have different molecular structure; visible light activated photochromic material 1, i.e., the naphthopyran analogue of the present invention, contains at least one carbazole group at Z1/Z2 position, while the material 2 is the naphthopyran analogue of the present invention without any carbazole group at Z1/Z2 position. The two materials showed different color after mobile flashlight excitation: visible light activated photochromic material 1 showed a broad absorption centred at 529 nm while visible light activated photochromic material 2 showed a broad absorption centered at 505 nm (FIG. 6).

The colors are adjusted by the molecular structures of compounds and thus their electronic transitions. The p-extended conjugation, heterocyclic ring or electron donating substituents would give rise to a minimized bandgap and therefore red-shifted absorption. For example, the visible light activated photochromic material 1 containing a methoxy group gives a more red-shifted color than photochromic material 2. Furthermore, the bleaching time is also affected by the molecular structures of compounds. A bulky group or moiety generally gives longer bleaching time to the compound.

Thus, the visible light activated photochromic compounds and formations for visible light activated ink have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "includes," "including," "comprises," and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A visible light activated ink comprising:
    a visible light activated photochromic compound in an amount of approximately 0.2 to 20 weight percent selected from one or more of 71-extended conjugation heterocyclic compounds of naphthopyran, benzopyran, spirooxazine, spiropyran, fulgide, diarylethene, and/or perimidinespirocyclohexadienone;
    one or more binders in an amount of approximately 10 to 45 weight percent;
    additives in an amount from approximately 2 to 8 weight percent, the additives including one or more surfactants; and
    a solvent in an amount of approximately 35 to 70 weight percent;
    wherein the visible light activated ink requires a visible light intensity of approximately 300 W/m$^2$ or greater at a wavelength of approximately 400-700 nm to produce a color change.

2. The visible light activated ink of claim 1, wherein the one or more binders is/are selected from one or more polymeric binders.

3. The visible light activated ink of claim 1, wherein the one or more surfactants is/are selected from one or both of polyethylene glycol sorbitan monolaurate and polyoxyethylenesorbitan monolaurate.

4. The visible light activated ink of claim 1, wherein the solvent is selected from one or more of water, alcohols, polyols, esters, ketones, glycerol, and/or vegetable oils.

5. The visible light activated ink of claim 1, wherein the π-extended conjugation heterocyclic compound of naphthopyran is represented by following formula:

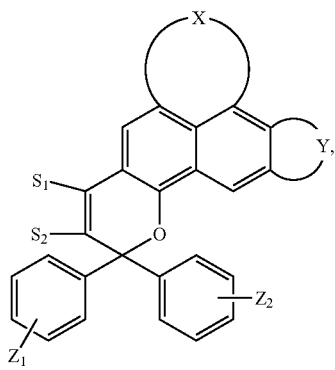

wherein X is selected from 1-alkylpiperidine-2,6-dione, 3,4-Dihydropyrido[1,2-a]benzimidazol-1(2H)-one, glutaric anhydride or 1-arylpipidine-2,6-dione;
Y is selected from hydrogen, benzene, naphthalene, fluorene, anthracene, phenanthrene, pyrene, tetracene, chrysene, pyrrolidine, pyrrole, pyrazole, carbazole, imidazole, benzimidazole, piperidine, indoline, pyridine, pyrazine, thiophene, benzo[b]thiophene, furan, benzofuran or any substituted analogues thereof;
$Z_1$ and $Z_2$ are independently selected from hydrogen, halo, halo alkyl, alkoxy, ester, ether, imide, diimide, nitro, cyano, carbonyl, sulfonyl group;
$S_1$ and $S_2$ are independently selected from hydrogen, halo, halo alkyl, ester, ether, imide, diimide, nitro, cyano, carbonyl, sulfonyl, benzene, naphthalene, fluorene, pyrrolidine, pyrrole, pyrazole, carbazole, imidazole, benzimidazole, piperidine, indoline, pyridine, pyrazine, thiophene, benzo[b]thiophene, furan, benzofuran or acetylene or any substituted analogues thereof.

6. The visible light activated ink of claim 1, wherein the π-extended conjugation heterocyclic compound of naphthopyran is represented by following formula:

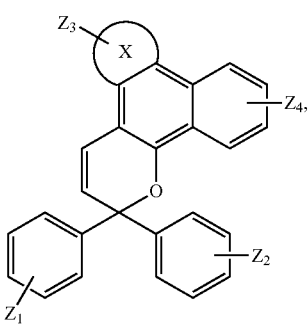

wherein X is selected from 3,3-di-alkyl-1,2-dihydroindene, benzene, naphthalene, fluorene, anthracene, phenanthrene, pyrene, tetracene, chrysene, pyrrolidine, pyrrole, pyrazole, carbazole, imidazole, benzimidazole, piperidine, indoline, pyridine, pyrazine, thiophene, benzo[b]thiophene, furan, benzofuran or any substituted analogues thereof;
$Z_1$, $Z_2$, $Z_3$ and $Z_4$ are independently selected from hydrogen, halo, halo alkyl, alkoxy, ester, ether, imide, diimide, nitro, cyano, carbonyl, or sulfonyl group.

7. The visible light activated ink of claim 1, wherein the π-extended conjugation heterocyclic compound of spirooxazine is represented by following formula:

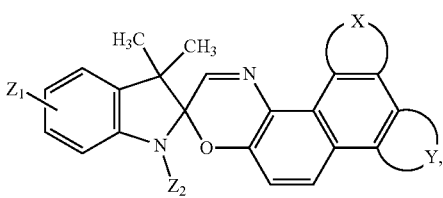

wherein X is selected from hydrogen, benzene, naphthalene, fluorene, anthracene, phenanthrene, pyrene, tetracene, chrysene, 1,10-phenanthroline, quinolone, pyrrolidine, pyrrole, pyrazole, imidazole, benzimidazole, piperidine, indoline, pyridine, pyrazine, thiophene, benzo[b]thiophene, furan or benzofuran;
Y is selected from 1,10-phenanthroline, pyrene, tetracene, chrysene, pyrrolidine, pyrrole, pyrazole, carbazole, imidazole, benzimidazole, piperidine, indoline, pyridine, pyrazine, thiophene, benzo[b]thiophene, furan or benzofuran;
$Z_1$ is selected from hydrogen, halo, halo alkyl, ester, imide, diimide, nitro, cyano, carbonyl, or a sulfonyl group; and
$Z_2$ is selected from unbranched or branched alkyl chains, benzene, phenol, anisole, or crown ether.

8. The visible light activated ink of claim 1, wherein the π-extended conjugation heterocyclic compound of spiropyran is represented by following formula:

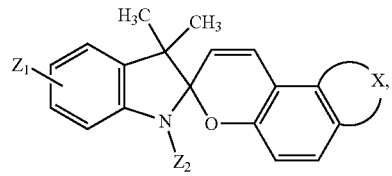

wherein X is selected from pyrazine, 1,10-phenanthroline, pyrene, tetracene, chrysene, pyrrolidine, pyrrole, pyrazole, carbazole, imidazole, benzimidazole, piperidine, indoline, pyridine, thiophene, benzo[b]thiophene, furan, benzofuran, or quinoline;
$Z_1$ is selected from hydrogen, halo, halo alkyl, ester, imide, diimide, nitro, cyano, carbonyl, or sulfonyl group; and
$Z_2$ is selected from unbranched or branched alkyl chains, benzene, phenol, anisole, or crown ether.

9. The visible light activated ink of claim 1, wherein the π-extended conjugation heterocyclic compound of fulgide is represented by following formula:

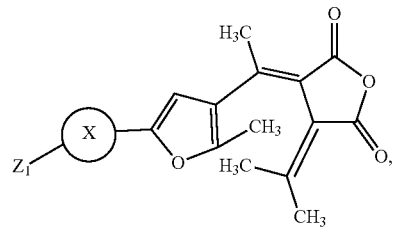

wherein X is selected from naphthalene, fluorene, anthracene, phenanthrene, pyrene, tetracene, chrysene, 1,10-phenanthroline, quinolone, pyrrolidine, pyrrole, pyrazole, carbazole, imidazole, benzimidazole, piperidine, indoline, pyridine, pyrazine, thiophene, benzo[b]thiophene, furan or benzofuran; and $Z_1$ is selected from hydrogen, halo, halo alkyl, ester, imide, diimide, nitro, cyano, carbonyl, or sulfonyl group.

10. The visible light activated ink of claim 1, wherein the π-extended conjugation heterocyclic compound of diarylethene is represented by following formula:

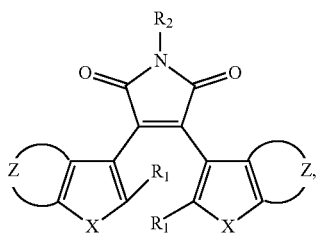

wherein X is selected from S, $SO_2$, N, O, P-aryl or O=P-aryl;

$R_1$ is selected from hydrogen atom, alkyl or alkoxy group;

$R_2$ is selected from hydrogen atom, alkyl, benzene, naphthalene, fluorene, anthracene, phenanthrene, pyrene, tetracene, chrysene, pyrrolidine, pyrrole, pyrazole, carbazole, imidazole, benzimidazole, piperidine, indoline, pyridine, pyrazine, thiophene, benzo[b]thiophene, furan or benzofuran;

Z is selected from hydrogen atoms, benzene, substituted benzene containing halogen, halo alkyl, ester, imide, diimide, nitro, cyano, carbonyl, or sulfonyl group.

11. The visible light activated ink of claim 1, wherein the π-extended conjugation heterocyclic compound of diarylethene is represented by following formula:

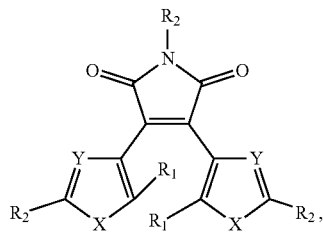

wherein X is selected from S, $SO_2$, N, O, P-aryl or O=P-aryl;

Y is selected from H, S, N, or O atom;

$R_1$ is selected from hydrogen atom, alkyl or alkoxy group;

$R_2$ is selected from hydrogen atom, alkyl, benzene, naphthalene, fluorene, anthracene, phenanthrene, pyrene, tetracene, chrysene, pyrrolidine, pyrrole, pyrazole, imidazole, benzimidazole, piperidine, indoline, pyridine, pyrazine, thiophene, benzo[b]thiophene, furan or benzofuran;

Z is selected from hydrogen atoms, benzene, substituted benzene containing halogen, halo alkyl, ester, imide, diimide, nitro, cyano, carbonyl, or sulfonyl group.

12. The visible light activated ink of claim 1, wherein the π-extended conjugation heterocyclic compounds of perimidinespirocyclohexadienone is represented by following formula:

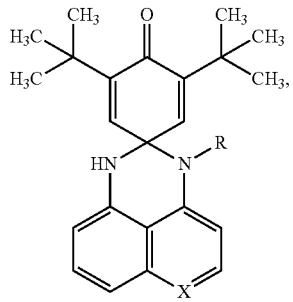

wherein X is selected from CH or N;

R is selected from hydrogen atom, aryl, arylalkyl, substituted aromatic cycles containing halogen, halo alkyl, ester, imide, diimide, nitro, cyano, carbonyl, or sulfonyl group.

13. The visible light activated ink of claim 1 wherein the binder is selected from one or more of rubbers, polyvinyl alcohol, styrene acrylic latex, polyurethane, acrylates, vinyl acrylates, vinyl acetates, methacrylates, styrene, acrylamides, methacrylamides, alkyds, phenolics, nitrocellulose, polyamides, poly(vinyl acetate), poly(vinyl butyral), and/or polyacrylics.

14. An ink composition selected from an inkjet ink composition, offset printing ink composition or coating ink composition, the ink composition comprising the visible light activated ink of claim 1, and optionally one or more resins, wherein the visible light activated photochromic compound has one of the following formulae:

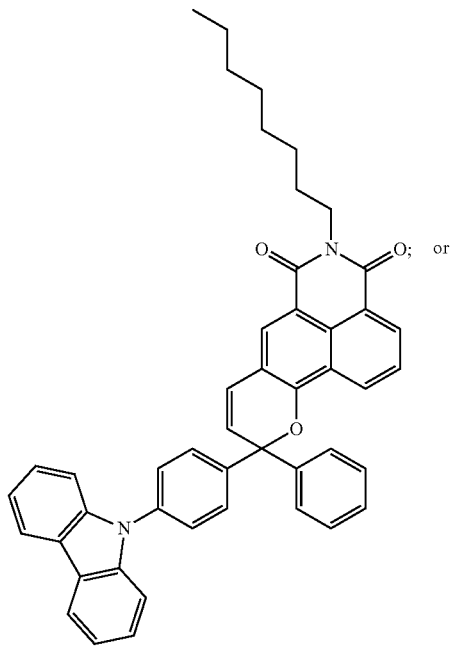

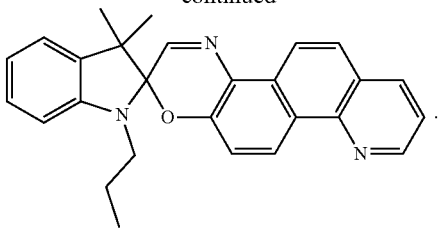

15. The ink composition of claim 14, wherein the visible light activated photochromic compound in the inkjet ink composition is in an amount of approximately 0.2 to 3 weight percent, and
wherein the inkjet ink composition further comprises the binder in an amount of approximately 30 to 40 weight percent selected from diethylene glycol monoethyl ethyl acetate and the solvent in an amount of approximately 50 to 70 weight percent selected from ethyl acetate.

16. The ink composition of claim 14, wherein the visible light activated photochromic compound in the offset printing ink composition is in an amount of approximately 1 to 20 weight percent, and
wherein the offset printing ink composition further comprises the additives in an amount of approximately 2 to 8 weight percent selected from one or more of polyethylene wax, rheological additives and Drier; the solvent in an amount of approximately 10 to 30% weight percent selected from one or more of linseed oil, soybean oil, tung oil and ethyl acetate; the one or more resins selected from rosin modified phenolic resin, polyurethane-based resin, rosin modified maleic acid resin, long-oil alkyd resin and mineral oil, in an amount of 25 to 90%.

17. The ink composition of claim 14, wherein the visible light activated photochromic compound in the coating ink composition is in an amount of approximately 0.3 to 5 weight percent, and
wherein the coating ink composition further comprises the solvent in an amount of approximately 10 to 55 weight percent selected from ethyl acetate; and the one or more resins is selected from polyurethane-based resin in an amount of 80 to 90 weight percent being doped with the visible light activated photochromic compound.

* * * * *